(12) United States Patent
Harada et al.

(10) Patent No.: US 6,900,335 B2
(45) Date of Patent: May 31, 2005

(54) PROCESS FOR PRODUCING 5-FLUOROOXINDOLE AND FOR PRODUCING INTERMEDIATES THEREFOR

(75) Inventors: Katsumasa Harada, Ube (JP); Shigeyoshi Nishino, Ube (JP); Kenji Hirotsu, Ube (JP); Shuji Yokoyama, Ube (JP); Takeshi Takahashi, Ube (JP); Hiroyuki Oda, Ube (JP)

(73) Assignee: Ube Industries, Ltd., Ube (JP)

( * ) Notice: Subject to any disclaimer, the term of this patent is extended or adjusted under 35 U.S.C. 154(b) by 12 days.

(21) Appl. No.: 10/333,316
(22) PCT Filed: Jul. 19, 2001
(86) PCT No.: PCT/JP01/06260
§ 371 (c)(1), (2), (4) Date: Jan. 16, 2003
(87) PCT Pub. No.: WO02/06228
PCT Pub. Date: Jan. 24, 2002

(65) Prior Publication Data
US 2003/0181731 A1 Sep. 25, 2003

(30) Foreign Application Priority Data

| Jul. 19, 2000 | (JP) | 2000-219161 |
| Aug. 8, 2000 | (JP) | 2000-239655 |
| Oct. 26, 2000 | (JP) | 2000-327345 |

(51) Int. Cl.$^7$ ........................................ C07D 209/34
(52) U.S. Cl. ....................................................... 548/486
(58) Field of Search ........................................ 548/486

(56) References Cited

U.S. PATENT DOCUMENTS

| 3,882,236 A | * | 5/1975 | Molloy | 514/418 |
| 4,160,032 A | * | 7/1979 | Hardtmann | 514/418 |
| 5,576,455 A | * | 11/1996 | Wang et al. | 558/406 |

FOREIGN PATENT DOCUMENTS

| EP | 0 208 510 A2 | 1/1987 |
| JP | 55-40616 A | 3/1980 |
| WO | WO 96/23770 A1 | 8/1996 |

OTHER PUBLICATIONS

G.J. Quallich et al, "A General Oxindole Synthesis", *SYNTHESIS*, pp. 51–53 (Jan. 1993).
E.A. Kraynack et al, "An Improved Procedure for the Regiospecific Synthesis of Electron Deficient 4– and 6–Substituted Isatins", *Tetrahedron Letters*, 39(42), pp. 7679–7682 (1998).

English translation of the International Preliminary Examination Report (5 pages) in the International Application PCT/JP01/06260.

* cited by examiner

Primary Examiner—Golam M M Shameem
(74) Attorney, Agent, or Firm—Frishauf, Holtz, Goodman & Chick, P.C.

(57) ABSTRACT

The present invention discloses a process for preparing 5-fluorooxindole represented by the formula (3):

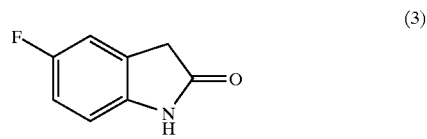

which comprises (A) a first step of cyclizing 2-(5-fluoro-2-nitrophenyl)malonic acid diester represented by the formula (1):

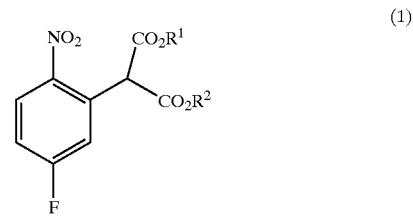

wherein $R^1$ and $R^2$ may be the same or different from each other and each represents a group which does not participate in the reaction, under reductive conditions to form 5-fluorooxindole-3-carboxylic acid ester represented by the formula (2):

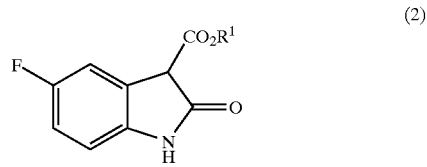

wherein $R^1$ has he same meaning as defined above, and (B) then, a second step of decarboxylating the 5-fluorooxindole-3-carboxylic acid ester, and a process for preparing its synthetic intermediates.

20 Claims, No Drawings

PROCESS FOR PRODUCING 5-FLUOROOXINDOLE AND FOR PRODUCING INTERMEDIATES THEREFOR

This application is a U.S. National Phase Application under 35 U.S.C. 371 of International Application No. PCT/JP01/0626 (not published in English) filed Jul. 19, 2001.

TECHNICAL FIELD

The present invention relates to a process for preparing 5-fluorooxindole and a process for preparing its preparation intermediates, more specifically to a process for preparing 5-fluorooxindole which is useful as a synthetic intermediate for a medicine such as an anticancer agent or anti-inflammatory and analgesic agent and a simple and easy process for preparing 2-(5-fluoro-2-nitrophenyl)-2-substituted acetic acid ester which is a preparation intermediate.

BACKGROUND ART

As a conventional method for preparing a 2-(5-halogeno-2-nitrophenyl)-2-substituted acetic acid ester compound from 2,4-dihalogenonitrobenzene compound, it has been known a method of synthesizing dimethyl 2-(5-halogeno-2-nitrophenyl)malonate by reacting dimethyl malonate with 2,4-dihalogenonitrobenzene in the presence of sodium hydride in dimethyl sulfoxide (Synthesis, 1993, 51). However, according to this method, complicated operations are required since sodium hydride having highly ignitable property is used and the reaction generates a hydrogen gas, so that it has problems as an industrial production process.

Also, as a process for producing 5-fluorooxindole from 2-(5-fluoro-2-nitrophenyl)malonic acid diester which is a kind of the above-mentioned 2-(5-halogeno-2-nitrophenyl)-2-substituted acetic acid ester, it has been described in Synthesis, 1993, 51, a process for producing 5-fluorooxindole by reacting lithium chloride with dimethyl 2-(5-fluoro-2-nitrophenyl)-malonate in a mixed solvent of water and dimethyl sulfoxide to once form methyl 5-fluoro-2-nitrophenylacetate, and then, reducing the resulting compound in acetic acid in the presence of iron and cyclizing the resulting compound. However, according to this process, there are problems that the reaction system is complicated and a total yield of the objective compound is as low as 49%.

An object of the present invention is to solve the above-mentioned problems and to provide an industrially suitable process for preparing 5-fluorooxindole from an easily available 2-(5-fluoro-2-nitrophenyl)malonic acid diester with a simple and easy method and a high yield.

A further object of the present invention is to solve the above-mentioned problems and to provide an industrially suitable process for preparing a 2-(5-halogeno-2-nitrophenyl)malonic acid diester compound from a 2,4-dihalogenonitrobenzene compound with a simple and easy method.

A still further object of the present invention is to provide a novel 5-fluorooxindole-3-carboxylic acid ester and a 2-(5-halogeno-2-nitrophenyl)-2-substituted acetic acid ester compound which are useful as synthetic intermediates of the above-mentioned preparation processes.

SUMMARY OF THE INVENTION

The present invention is to provide a process for preparing 5-fluorooxindole represented by the formula (3):

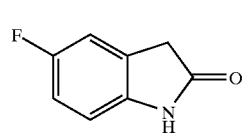

(3)

which comprises (A) a first step of cyclizing 2-(5-fluoro-2-nitrophenyl)malonic acid diester represented by the formula (1):

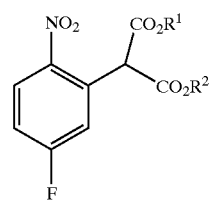

(1)

wherein $R^1$ and $R^2$ may be the same or different from each other and each represents a group which does not participate in the reaction,
under reductive conditions to form 5-fluorooxindole-3-carboxylic acid ester represented by the formula (2):

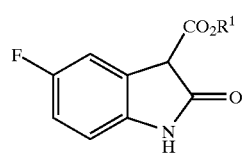

(2)

wherein $R^1$ has the same meaning as defined above, and (B) then, a second step of decarboxylating the 5-fluorooxindole-3-carboxylic acid ester.

The present invention also provides 5-fluorooxindole-3-carboxylic acid ester represented by the formula (2):

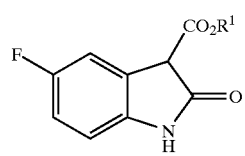

(2)

wherein $R^1$ represents a group which does not participate in the reaction.

The present invention also provides a process for preparing a 2-(5-halogeno-2-nitrophenyl)-2-substituted acetic acid ester compound represented by the formula (6):

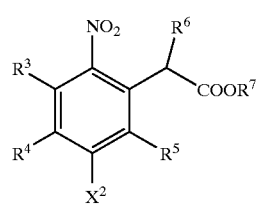

(6)

wherein $R^3$, $R^4$ and $R^5$ each represents a group which does not participate in the reaction, $R^6$ represents an alkoxycarbonyl group, an aralkyloxycarbonyl group, an aryloxycarbonyl group, an acyl group or a cyano group, $R^7$ represents a group which does not participate in the reaction, and $X^2$ represents a halogen atom, which comprises reacting a 2,4-dihalogenonitrobenzene compound represented by the formula (4):

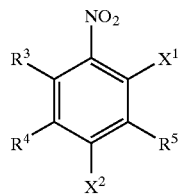
(4)

wherein $R^3$, $R^4$, $R^5$, and $X^2$ have the same meanings as defined above and $X^1$ represents a halogen atom, with a 2-mono-substituted acetic acid ester compound represented by the formula (5):

(5)

wherein $R^6$ and $R^7$ have the same meanings as defined above,
in the presence of a metal alkoxide (s) or a metal inorganic acid salt(s) and in an organic solvent(s).

The present invention further provides a 2-(5-halogeno-2-nitrophenyl)-2-acylacetic acid ester compound represented by the formula (7):

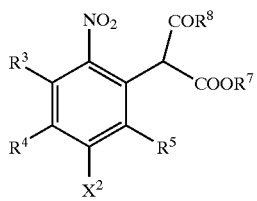
(7)

wherein $R^3$, $R^4$, $R^5$, $R^7$ and $X^2$ have the same meanings as defined above, and $R^8$ represents an alkyl group, an aralkyl group or an aryl group,
and a 2-(5-halogeno-2-nitrophenyl)-2-cyanoacetic acid ester compound represented by the formula (8):

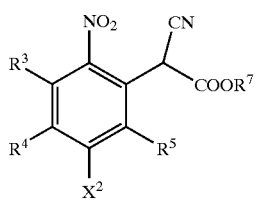
(8)

wherein $R^3$, $R^4$, $R^5$, $R^7$ and $X^2$ have the same meanings as defined above.

BEST MODE FOR CARRYING OUT THE INVENTION

The process for preparing 5-fluorooxindole of the present invention comprises two steps of (A) a first step of cyclizing a 2-(5-fluoro-2-nitrophenyl)-malonic acid diester represented by the formula (1) under reductive conditions to form a 5-fluorooxindole-3-carboxylic acid ester represented by the formula (2), and
(B) then, a second step of decarboxylating the 5-fluorooxindole-3-carboxylic acid ester, to obtain 5-fluorooxindole as a reaction product.

Subsequently, the above two steps are explained successively.

(A) The First Step

The first step of the present invention is a step of cyclizing 2-(5-fluoro-2-nitrophenyl)malonic acid diester represented by the formula (1) under reductive conditions to obtain 5-fluorooxindole-3-carboxylic acid ester represented by the formula (2).

The 2-(5-fluoro-2-nitrophenyl)malonic acid diester to be used in the first step of the present invention is represented by the above-mentioned formula (1). In the formula (1), $R^1$ and $R^2$ maybe the same or different from each other, and each represents a group which does not participate in the reaction, more specifically, there may be mentioned, for example, an alkyl group, a cycloalkyl group, an aralkyl group or an aryl group.

As the above-mentioned alkyl group, an alkyl group having 1 to 10 carbon atoms is particularly preferred, and there may be mentioned, for example, a methyl group, an ethyl group, a propyl group, a butyl group, a pentyl group, a hexyl group, a heptyl group, an octyl group, a nonyl group, a decyl group and the like. These groups may include various kinds of isomers.

As the above-mentioned cycloalkyl group, a cycloalkyl group having 3 to 7 carbon atoms is particularly preferred, and there may be mentioned, for example, a cyclopropyl group, a cyclobutyl group, a cyclopentyl group, a cyclohexyl group, a cycloheptyl group and the like. These groups may include various kinds of isomers.

As the above-mentioned aralkyl group, an aralkyl group having 7 to 10 carbon atoms is particularly preferred, and there may be mentioned, for example, abenzyl group, aphenethyl group, a phenylpropyl group and a phenylbutyl group. These groups may include various kinds of isomers.

As the above-mentioned aryl group, an aryl group having 6 to 14 carbon atoms is particularly preferred, and there may be mentioned, for example, a phenyl group, a tolyl group, a naphthyl group, an anthranyl group and the like. These groups may include various kinds of isomers.

The first step of the present invention is not specifically limited so long as it is a reductive method generally carried out, and it is preferably carried out in the presence of a catalyst under hydrogen atmosphere.

As the above-mentioned catalyst, there may be mentioned those containing at least one metal atom selected from the group consisting of palladium, platinum and nickel, more specifically there may be mentioned, for example, palladium/carbon, palladium/barium sulfate, palladium hydroxide/carbon, platinum/carbon, palladium-platinum/carbon, platinum oxide, Raney nickel and the like, and palladium/carbon is preferably used.

An amount of the above-mentioned catalyst to be used is preferably 0.01 to 1.0% by weight, more preferably 0.05 to 0.5% by weight in terms of a metal atom based on the amount of 2-(5-fluoro-2-nitrophenyl)malonic acid diester. Incidentally, these catalysts may be used singly or in combination of two or more.

The first step of the present invention is preferably carried out in the presence of a solvent. As the solvent to be used, it is not specifically limited so long as it does not inhibit the reaction, and there may be mentioned water; alcohols such as methanol, ethanol and the like; esters such as methyl acetate, ethyl acetate and the like; aromatic hydrocarbons such as benzene, toluene and the like; ethers such as tetrahydrofuran, dioxane and the like, and preferably water, alcohols and/or ethers is/are used, more preferably water, methanol and/or ethanol is/are used.

An amount of the above-mentioned solvent to be used is optionally controlled depending on uniformity or stirrability of the solution, and is preferably 3 to 50-fold weight, more preferably 5 to 30-fold weight based on the amount of 2-(5-fluoro-2-nitrophenyl)malonic acid diester. Incidentally, these solvents may be used singly or in combination of two or more.

The first step of the present invention is carried out, for example, in a hydrogen atmosphere, by mixing 2-(5-fluoro-2-nitrophenyl)malonic acid diester, a catalyst and a solvent and stirring them and the like. A reaction pressure at that time is preferably 0.1 to 5 MPa, more preferably 0.1 to 2 MPa, and a reaction temperature is preferably 20 to 80° C., more preferably 30 to 60° C.

In the first step of the present invention, a solution containing 5-fluorooxindole-3-carboxylic acid ester as a main product can be obtained, and in the present invention, it is generally carried out, after separation of the catalyst, if necessary, the next step by using said solution as such or after subjecting to concentration. However, in some cases, the formed 5-fluorooxindole-3-carboxylic acid ester is once isolated by a general method such as recrystallization, distillation, column chromatography and the like, and then, the next step may be carried out.

Also, 5-fluorooxindole-3-carboxylic acid ester (a keto form) represented by the formula (2):

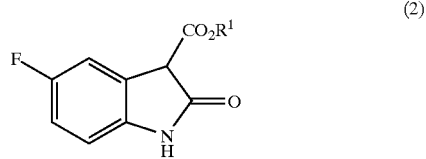

(2)

wherein $R^1$ has the same meaning as defined above, obtained in the first step of the present invention is a novel compound useful as an intermediate for 5-fluorooxindole.

Incidentally, in the solution, it is a case where it becomes equilibrium with an enol form represented by the formula (2'):

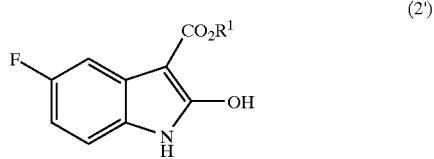

(2')

wherein $R^1$ has the same meaning as defined above.
(B) The Second Step

The second step of the present invention is a step of decarboxylating the 5-fluorooxindole-3-carboxylic acid ester represented by the formula (2) obtained in the first step to obtain 5-fluorooxindole.

The second step of the present invention is not particularly limited so long as it is a decarboxylation method usually carried out, and it is preferably carried out in the presence of an acid.

As the above-mentioned acid, there may be mentioned hydrochloric acid, sulfuric acid, nitric acid, methanesulfonic acid, acetic acid and the like, and hydrochloric acid or sulfuric acid is preferably used.

As an amount of the above-mentioned acid to be used, it is preferably used in an amount of 1 to 10-fold mole, more preferably 2 to 5-fold mole based on the amount of the 5-fluorooxindole-3-carboxylic acid ester. Incidentally, these acids may be used singly or in combination of two or more.

The second step of the present invention is preferably carried out in the presence of a solvent(s). As the solvent to be used, it is not specifically limited so long as it does not inhibit the reaction, and there may be mentioned water; alcohols such as methanol, ethanol, n-butyl alcohol, t-butyl alcohol and the like, ethers such as tetrahydrofuran, dioxane and the like; hydrocarbons such as cyclohexane, toluene and the like, and preferably water, alcohols and/or ethers is/are used, more preferably water, methanol and/or ethanol is/are used.

An amount of the above-mentioned solvent may be optionally controlled depending on the uniformity or stirrability of the solution, and preferably 2 to 20-fold weight, more preferably 4 to 10-fold weight based on the amount of the 5-fluorooxindole-3-carboxylic acid ester. Incidentally, these solvents may be used singly or in combination of two or more.

The second step of the present invention is carried out, for example, in an inert gas atmosphere, by mixing 5-fluorooxindole-3-carboxylic acid ester obtained in the first step or a reaction mixture containing the same, an acid(s) and a solvent(s), and stirring the mixture and the like. A reaction temperature at that time is preferably 20 to 110° C., more preferably 50 to 90° C., and are action pressure is not specifically limited.

The 5-fluorooxindole obtained in the second step of the present invention is separated and purified by a general method such as recrystallization, distillation, column chromatography and the like.

Next, a process for preparing the 2-(5-halogeno-2-nitrophenyl)malonic acid diester compound which is a starting compound in the above-mentioned reaction of the present invention is explained.

The 2,4-dihalogenonitrobenzene compound to be used in the reaction of the present invention is represented by the above-mentioned formula (4). In the formula (4), $R^3$, $R^4$ and $R^5$ are groups which do not participate in the reaction, and more specifically, they each represent a hydrogen atom; a halogen atom; an alkyl group, a cycloalkyl group, an aralkyl group, an aryl group, an alkoxy group or an aryloxy group each of which may have a substituent(s).

As the above-mentioned halogen atom, there may be mentioned a fluorine atom, a chlorine atom, a bromine atom and an iodine atom.

As the above-mentioned alkyl group, an alkyl group having 1 to 10 carbon atoms is particularly preferred, and there may be mentioned, for example, a methyl group, an ethyl group, a propyl group, a butyl group, a pentyl group, a hexyl group, a heptyl group, an octyl group, a nonyl group, a decyl group and the like. These alkyl groups may include various isomers.

As the above-mentioned cycloalkyl group, a cycloalkyl group having 3 to 7 carbon atoms is particularly preferred, and there may be mentioned, for example, a cyclopropyl group, a cyclobutyl group, a cyclopentyl group, a cyclohexyl group, a cycloheptyl group and the like. These cycloalkyl groups may include various kinds of isomers.

As the above-mentioned aralkyl group, an aralkyl group having 7 to 10 carbon atoms is particularly preferred, and there may be mentioned, for example, a benzyl group, a phenethyl group, a phenylpropyl group, a phenylbutyl group and the like. These aralkyl groups may include various kinds of isomers.

As the above-mentioned aryl group, aryl group having 6 to 14 carbon atoms is particularly preferred, and there may be mentioned, for example, a phenyl group, a tolyl group, a naphthyl group, an anthranyl group and the like. These aryl groups may include various kinds of isomers.

As the above-mentioned alkoxy group, an alkoxy group having 1 to 12 carbon atoms is particularly preferred, and there maybe mentioned, for example, a methoxy group, an ethoxy group, a propoxy group, a butoxy group, a benzyloxy group and the like. These alkoxy groups may include various kinds of isomers.

As the above-mentioned aryloxy group, an aryloxy group having 6 to 14 carbon atoms is particularly preferred, and there may be mentioned, for example, a phenoxy group, a tolyloxy group and the like. These aryloxy groups may include various kinds of isomers.

The above-mentioned alkyl group, cycloalkyl group, aralkyl group, aryl group, alkoxy group or aryloxy group may have a substituent(s). As the substituent(s), there may be mentioned at least one selected from a substituent formed through a carbon atom, a substituent formed through an oxygen atom and a substituent formed through a nitrogen atom.

As the above-mentioned substituent formed through a carbon atom, there may be mentioned, for example, an alkyl group such as a methyl group, an ethyl group, a propyl group and the like; an aralkyl group such as a benzyl group and the like; an aryl group such as a phenethyl group and the like; and a cyano group.

As the above-mentioned substituent formed through an oxygen atom, there may be mentioned, for example, an alkoxy group such as a methoxy group, an ethoxy group, a propoxy group, a butoxy group, a benzyloxy group and the like; an aryloxy group such as a phenoxy group and the like.

As the above-mentioned formed through a nitrogen atom, there may be mentioned, for example, a nitro group; and an amino group.

Also, in the formula (1), $X^1$ and $X^2$ both represent a halogen atom, and there may be mentioned a fluorine atom, a chlorine atom, a bromine atom and an iodine atom.

The 2-mono-substituted acetic acid ester compound to be used in the reaction of the present invention is represented by the above-mentioned formula (5). In the formula (5), $R^6$ represents an alkoxycarbonyl group such as a methoxycarbonyl group, an ethoxycarbonyl group, a propoxycarbonyl group, a butoxycarbonyl group and the like; an aralkyloxycarbonyl group such as a benzyloxycarbonyl group and the like; an aryloxycarbonyl group such as a phenoxycarbonyl group and the like; an acyl group such as an acetyl group, a propionyl group, a benzoyl group and the like; and a cyano group. These groups may include various kinds of isomers. $R^7$ is a group which does not participate in the reaction, and more specifically, there may be mentioned an alkyl group having 1 to 4 carbon atoms such as a methyl group, an ethyl group, a propyl group and the like; an aralkyl group such as a benzyl group and the like; and an aryl group such as a phenyl group and the like. These groups may include various kinds of isomers.

An amount of the above-mentioned 2-mono-substituted acetic acid ester compound is preferably 1.0 to 5.0-fold mole, more preferably 1.2 to 3.0-fold mole based on the amount of the 2,4-dihalogenonitrobenzene compound.

As a metal atom of the metal alkoxide to be used in the reaction of the present invention, there may be mentioned, for example, a Group 1A atom (Group 1 atom) such as a lithium atom, a sodium atom, a potassium atom and the like; a Group 2A atom (Group 2 atom) such as a magnesium atom, a calcium atom and the like; and a Group 3B atom (Group 13 atom) such as aluminum and the like as described in Rikagaku Jiten (Science and Chemistry Dictionary), fourth edition (published by Iwanami Shoten, Japan).

As the above-mentioned metal alkoxide(s), there may be used, for example, a Group 1A metal (Group 1 metal) alkoxide such as lithiummethoxide, sodiummethoxide, potassiummethoxide, sodium ethoxide, potassium ethoxide, potassium t-butoxide and the like; a Group 2A metal (Group 2 metal) alkoxide such as magnesium methoxide, calcium methoxide and the like; a Group 3B metal (Group 13 metal) alkoxide such as aluminum isopropoxide and the like.

Also, as a metal atom of the metal inorganic acid salt to be used in the reaction of the present invention, there may be mentioned, for example, an alkali metal atom such as a lithium atom, a sodium atom, a potassium atom and the like; an alkaline earth metal atom such as a magnesium atom, a calcium atom and the like, preferably an alkali metal atom, more preferably a sodium atom or a potassium atom.

As an inorganic acid of the metal inorganic acid salt to be used in the reaction of the present invention, there may be mentioned, for example, carbonic acid, phosphoric acid and the like, preferably carbonic acid.

As the above-mentioned metal inorganic acid salt(s), there may be mentioned, for example, sodium carbonate, sodium hydrogen carbonate, potassium carbonate, potassium hydrogen carbonate, magnesium carbonate, calcium carbonate, sodium phosphate and sodium hydrogen phosphate, and sodium carbonate or potassium carbonate is preferably used.

An amount of the above-mentioned metal alkoxide(s) or metal inorganic acid salt(s) is preferably 1.0 to 5.0-fold mole, more preferably 1.2 to 3.0-fold mole based on the amount of the 2,4-dihalogenonitrobenzene compound. These metal alkoxides or metal inorganic acid salts may be used singly or in combination of two or more.

As the organic solvent(s) to be used in the reaction of the present invention, it is not specifically limited so long as it does not inhibit the reaction, and there may be mentioned, for example, ethers such as diethyl ether, diisopropyl ether, tetrahydrofuran, dioxane and the like; aliphatic hydrocarbons such as hexane, cyclohexane and the like; aromatic hydrocarbons such as benzene, toluene, xylene and the like; amides such as N,N-dimethylformamide, N,N'-dimethylimidazolidinone and the like; nitriles such as acetonitrile, propionitrile and the like; dimethyl sulfoxide and the like. It is preferably aliphatic hydrocarbons, aromatic hydrocarbons, amides or dimethyl sulfoxide when a metal alkoxide is used, and aliphatic hydrocarbons, aromatic hydrocarbons, amides, nitriles or dimethyl sulfoxide when a metal inorganic acid salt is used, and it is more preferably cyclohexane, toluene, N,N-dimethylformamide or dimethyl sulfoxide when a metal alkoxide is used, and cyclohexane, toluene, acetonitrile or N,N-dimethylformamide when a metal inorganic acid salt is used.

An amount of the above-mentioned organic solvent may be optionally controlled depending on uniformity or stirrability of the reaction mixture, and it is preferably 1 to 50-fold weight, more preferably 1.5 to 20-fold weight based on the amount of the 2,4-dihalogenonitrobenzene compound. These organic solvents may be used singly or in combination of two or more.

The reaction of the present invention can be carried out, for example, by mixing the 2,4-dihalogenonitrobenzene compound, the 2-mono-substituted acetic acid ester compound, at least one of the metal alkoxide and the metal inorganic acid salt, and the organic solvent and they are reacted. As a preferred embodiment of the present invention, the 2-mono-substituted acetic acid ester compound, at least one of the metal alkoxide and the metal inorganic acid salt, and an organic solvent are mixed, and the 2,4-dihalogenonitrobenzene compound is added to the above mixture preferably at 20 to 140° C., more preferably at 30 to 120° C. (if necessary, after removing a formed alcohol by single distillation or azeotropic distillation under the pressure of 0.001 to 0.1 MPa, or while removing the same) to effect the reaction. Also, when the metal inorganic acid salt is used, the reaction may be promoted by adding crown ether or polyethylene glycol.

The 2-(5-halogeno-2-nitrophenyl)-2-substituted acetic acid ester compound which is an objective compound obtained by the reaction of the present invention can be separated and purified by a general method such as column chromatography, distillation, recrystallization and the like after completion of the reaction.

Incidentally, a 2-(5-halogeno-2-nitrophenyl)-2-acylacetic acid ester compound represented by the formula (7):

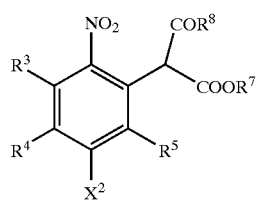

(7)

wherein $R^3$, $R^4$, $R^5$, $R^7$, $R^8$ and $X^2$ have the same meanings as defined above,
and a 2-(5-halogeno-2-nitrophenyl)-2-cyanoacetic acid ester compound represented by the formula (8):

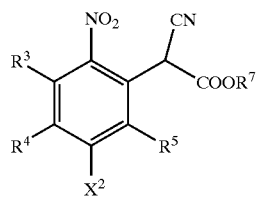

(8)

wherein $R^3$, $R^4$, $R^5$, $R^7$ and $x^2$ have the same meanings as defined above,
are novel compounds.

EXAMPLE

Next, the present invention will be explained by referring to Examples, but the scope of the present invention is not limited by these.

Example 1

In a flask made of glass equipped with a stirrer, a thermometer, a distillation device and a dropping funnel and having an inner volume of 200 ml were charged 3.40 g (62.9 mmol) of sodium methoxide and 30 ml dimethyl sulfoxide under argon atmosphere, and then, while stirring at room temperature, 8.48 g (62.9 mmol) of dimethyl malonate with a purity of 98% was gradually added dropwise over 5 minutes. Moreover, 10 ml of cyclohexane was added to the mixture, and after raising the temperature to 100 to 105° C., the formed methanol was subjected to azeotropic distillation (removed by distillation) with cyclohexane. After this operation (removal of methanol by distillation) was repeated twice, the reaction mixture was cooled to 70° C., and 5.10 g (31.4 mmol) of 2,4-difluoro-nitrobenzene with a purity of 98% was gradually added dropwise over 10 minutes, and the resulting mixture was reacted at 70 to 80° C. for one hour. After completion of the reaction, the mixture was cooled to room temperature, 100 ml of toluene was added to the mixture and 5.25 ml (31.4 mmol) of 6 mol/l hydrochloric acid was gradually added dropwise while stirring. Then, the organic layer was separated, and the resulting mixture was washed successively with 50 ml of water and 50 ml of a saturated saline solution in this order, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=9:1 (volume ratio)) to obtain 5.60 g of dimethyl 2-(5-fluoro-2-nitrophenyl)malonate (isolation yield: 64%) as white crystals with a purity of 98% (areal percentage by high performance liquid chromatography)

Physical properties of the dimethyl 2-(5- fluoro-2-nitrophenyl)malonate were as follows.

EI-MS (m/e) ; 225 (M-NO$_2$) , CI-MS (m/e); 272 (M+1)
$^1$H-NMR (CDCl$_3$, δ (ppm)); 3.82 (6H, s), 5.40 (1H, s), 7.20 to 7.35 (2H, m), 8.1 to 8.2 (1H, m)

Example 2

In a flask made of glass equipped with a stirrer, a thermometer, a distillation device and a dropping funnel and having an inner volume of 500 ml were charged 11.0 g (0.2 mol) of sodium methoxide and 30 ml of dimethyl sulfoxide under argon atmosphere, and the temperature of the mixture was raised to 110 to 120° C. while stirring, then, 27.0 g (0.2 mol) of dimethyl malonate with a purity of 98% was gradually added dropwise to the mixture over 30 minutes, and the resulting mixture was stirred for 2 hours while removing methanol under reduced pressure of 0.010 to 0.013 MPa. Subsequently, the mixture was cooled to 100° C. under the same pressure, 16.2 g (0.1 mol) of 2,4-difluoronitrobenzene with a purity of 98% was gradually added dropwise to the mixture over 30 minutes, and the mixture was further reacted at the same pressure and the same temperature for one hour. After completion of the reaction, the mixture was cooled to room temperature, 100 ml of toluene was added to the mixture and 40 ml (0.2 mol) of 5 mol/l hydrochloric acid was gradually added dropwise to the mixture while stirring. Then, the organic layer was separated, and washed successively with 50 ml of water and 50 ml of a saturated saline solution in this order, and dried over anhydrous magnesium sulfate. This organic layer was analyzed (absolute quantitative method) by high performance liquid chromatography, it can be found that 20.6 g (yield: 76%) of dimethyl 2-(5-fluoro-2-nitrophenyl)malonate was formed.

Example 3

In a flask made of glass equipped with a stirrer, a thermometer, a reflux condenser and a dropping funnel and having an inner volume of 100 ml were charged 3.40 g (62.9 mmol) of sodium methoxide and 20 ml of dimethyl sulfoxide under argon atmosphere, and then, while stirring at room temperature, 8.31 g (62.3 mmol) of dimethyl malonate with a purity of 99% was gradually added dropwise to the mixture over 5 minutes. After cooling the mixture to 20° C., 5.10 g (31.4 mmol) of 2,4-di-fluoronitrobenzene was gradually added dropwise to the mixture over 5 minutes, and the temperature of the mixture was raised to 80° C. and the mixture was reacted for one hour. After completion of the reaction, the mixture was cooled to room temperature, and then, 100 ml of ethyl acetate was added to the mixture, and 5.25 ml (31.4 mmol) of 6 mol/l hydrochloric acid was gradually added dropwise to the mixture while stirring. Then, the organic layer was separated, and washed successively with 30 ml of water and 30 ml of a saturated saline solution in this order, and dried over anhydrous magnesium sulfate. After filtration, the filtrate was concentrated under reduced pressure and the resulting concentrate was purified by silica gel column chromatography (filler: Daisogel 1002W, eluent: hexane:ethyl acetate=9:1 (volume ratio)) to obtain 6.55 g of dimethyl 2-(5-fluoro-2-nitrophenyl) malonate (isolation yield: 75%) as a white crystal with a purity of 97.2% (areal percentage by high performance liquid chromatography).

Example 4

In a similar device as in Example 1 were charged 3.40 g (62.9 mmol) of sodium methoxide and 30 ml of dimethyl sulfoxide under argon atmosphere, then, while stirring at room temperature, 6.30 g (62.9 mmol) of methyl cyanoacetate with a purity of 99% was gradually added dropwise over 5 minutes. Moreover, 10 ml of cyclohexane was added to the mixture, and the temperature of the mixture was raised to 100 to 105° C., formed methanol was subjected to distillation (azeotropic distillation) with cyclohexane. This operation (distillation of methanol) was repeated twice, then, the mixture was cooled to room temperature, 5.10 g (41.9 mmol) of 2,4-difluoronitrobenzene with a purity of 98% was gradually added dropwise to the mixture over 10 minutes while maintaining the temperature to 30 to 40° C., and the resulting mixture was reacted by raising the temperature to 75° C. for one hour. After completion of the reaction, the mixture was cooled to room temperature, then, 100 ml of ethyl acetate was added to the mixture, and 5.25 ml (31.4 mmol) of 6 mol/l hydrochloric acid was gradually added dropwise to the mixture while stirring. Then, the organic layer was separated, and washed successively with 50 ml of water and 50 ml of a saturated saline solution in this order, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=9:1 (volume ratio)) to obtain 5.48 g of methyl 2-(5-fluoro-2-nitrophenyl)-2-cyanoacetate (isolation yield: 71%) as a yellowish oily product with a purity of 97% (areal percentage by high performance liquid chromatography).

Methyl 2-(5-fluoro-2-nitrophenyl)-2-cyanoacetate is a novel compound having the following physical properties.

EI-MS (m/e) ; 192 (M-NO$_2$), CI-MS (m/e) ; 239 (M+1) FT-IR (liquid film method, cm$^{-1}$) ; 3300 to 2800, 2255, 1758, 1594, 1533, 1347, 1262, 1222 $^1$H-NMR (CDCl$_3$, δ (ppm)); 3.88 (3H, s), 5.71 (1H, s), 7.3 to 7.4 (1H, m), 7.45 to 7.55 (1H, m), 8.3 to 8.4 (1H, m)

Example 5

In the similar device as in Example 3 were charged 6.98 g (62.2 mmol) of potassium t-butoxide and 15 ml of dimethyl sulfoxide under argon atmosphere, and then, 7.30 ml (62.2 mmol) of methyl acetoacetate with a purity of 99% was gradually added dropwise to the mixture over 5 minutes while stirring under ice-cooling. The temperature of the mixture was raised to 25 to 30° C., and after stirring for 15 minutes, 5.00 g (30.8 mmol) of 2,4-difluoronitrobenzene with a purity of 98% was gradually added dropwise to the mixture over 10 minutes, and the mixture was reacted at 40 to 45° C. for 15 minutes, and further at 50 to 55° C. for 1.5 hours. After completion of the reaction, the mixture was cooled to room temperature, 100ml of ethyl acetate was added to the mixture, and 5.13 ml (30.7 mmol) of 6 mol/l hydrochloric acid and 20 ml of water were gradually added dropwise to the mixture while stirring. Then, the organic layer was separated, and washed with 30 ml of a saturated saline solution, and dried over anhydrous magnesium sulfate. After filtration, the filtrate was concentrated under reduced pressure, and the resulting concentrate was purified by silica gel column chromatography (filler: Daisogel 1002W, eluent: toluene) to obtain 6.40 g (isolation yield: 75%, keto form : enol form=1:6.5) of methyl 2-(5-fluoro-2-nitrophenyl)-2-acetoacetate as a yellowish oily product with a purity of 92% (areal percentage by high performance liquid chromatography).

Methyl 2-(5-fluoro-2-nitrophenyl)-2-acetoacetate is a novel compound having the following physical properties.

EI-MS (m/e) ; 213 (M-CH$_2$CO), CI-MS (m/e) ; 256 (M+1) FT-IR (liquid film method, cm$^{-1}$) ; 3400 to 2300, 1736, 1655, 1619, 1527, 1445, 1347, 1280, 1250, 1066, 884, 836 $^1$H-NMR (CDCl$_3$, δ (ppm)); keto form: 2.42 (3H, s), 3.81 (3H, s), 5.43 (1H, s), 7.10 to 8.25 (3H, m) enol form: 1.87 (3H, s), 3.65 (3H, s), 6.95 to 7.05 (1H, m), 7.10 to 7.25 (1H, m), 8.05 to 8.20 (1H, m), 12.90 (1H, s)

Example 6

In a flask made of glass equipped with a stirrer, a thermometer, a reflux condenser and a dropping funnel and having an inner volume of 200 ml were charged 2.79 g (51.6 mmol) of sodium methoxide and 15 ml of dimethyl sulfoxide under argon atmosphere, and then, while stirring at room temperature, 5.16 g (51.6 mmol) of methyl cyanoacetate with a purity of 99% was gradually added dropwise over 5 minutes. Moreover, at room temperature, to the mixture was gradually added dropwise 5.00 g (25.8 mmol) of 2,4-dichloronitrobenzene with a purity of 98%, and the resulting mixture was reacted at 40 to 48° C. for 10 minutes and at 65° C. for 2 hours. After completion of the reaction, the mixture was cooled to room temperature, 100 ml of ethylacetate was added to the mixture, and 4.30 ml (25.7 mmol) of 6 mol/l hydrochloric acid and 20 ml water were gradually added dropwise while stirring. Then, the organic layer was separated, washed with 50 ml of a saturated saline solution, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=9:1 (volume ratio)) to obtain 6.11 g (isolation yield: 92%) of methyl 2-(5-chloro-2-nitrophenyl)-2-cyanoacetate as yellowish crystals with a purity of 99% (areal percentage by high performance liquid chromatography).

Methyl 2-(5-chloro-2-nitrophenyl)-2-cyanoacetate is a novel compound having the following physical properties.

Melting point; 98 to 100° C. EI-MS (m/e) ; 210, 208 (M-NO$_2$), CI-MS (m/e) ; 257, 255 (M+1) Elemental analysis; Carbon 47.17%, Hydrogen 2.73%, Nitrogen 10.98% (theoretical value (C$_{10}$H$_7$N$_2$O$_4$Cl) ; Carbon 47.17%, Hydrogen 2.77%, Nitrogen 11.00%) FT-IR (KBr method, cm$^{-1}$) ;

3200 to 2800, 2247, 1764, 1575, 1524, 1342, 1270, 1220, 850 $^1$H-NMR (CDCl$_3$, δ (ppm)); 3.88 (3H, s), 5.68 (1H, s), 7.62 (1H, dd, J=2.2, 8.8 Hz), 7.77 (1H, d, J=2.2Hz), 8.21 (1H, d, J=8.8Hz)

Example 7

In a flask made of glass equipped with a stirrer, a thermometer, a reflux condenser and a dropping funnel and having an inner volume of 100 ml were charged 6.98 g (62.2 mmol) of potassium t-butoxide and 15 ml of dimethyl sulfoxide under argon atmosphere, and then, 7.30 g (62.2 mmol) of methyl acetoacetate with a purity of 99% was gradually added dropwise to the mixture over 5 minutes under ice-cooling and stirring. The temperature of the mixture was raised to 25 to 30° C., and after stirring for 15 minutes, 5.97 g (30.8 mmol) of 2,4-di-chloronitrobenzene with a purity of 99% was gradually added dropwise to the mixture, and the mixture was reacted at 65 to 70° C. for 3 hours. After completion of the reaction, the mixture was cooled to room temperature, then, 100 ml of ethyl acetate was added to the mixture, and 5.13 ml (30.7 mmol) of 6 mol/l hydrochloric acid and 20 ml of water were gradually added dropwise to the mixture while stirring. Then, the organic layer was separated, and washed successively with 20 ml of water and 30 ml of a saturated saline solution in this order, and dried over anhydrous magnesium sulfate. After filtration, the filtrate was concentrated under reduced pressure, and the resulting concentrate was purified by silica gel column chromatography (filler: Daisogel 1002W, eluent: toluene) to obtain 6.40 g of methyl 2-(5-chloro-2-nitrophenyl)-2-acetoacetate (isolation yield: 73%, keto form : enol form=1:8.5) as a yellowish oily product with a purity of 95% (areal percentage by high performance liquid chromatography).

Methyl 2-(5-chloro-2-nitrophenyl)-2-acetoacetate is a novel compound having the following physical properties.

EI-MS (m/e) ; 231 (M-CH$_2$CO), CI-MS (m/e) ; 274, 272 (M+1) FT-IR (liquid film method, cm$^{-1}$) ; 3400 to 2500, 1659, 1618, 1526, 1444, 1346, 1266, 1227, 858, 836 $^1$H-NMR (CDCl$_3$, δ (ppm)); Keto form: 2.42 (3H, s), 3.81 (3H, s), 5.34 (1H, s), 7.4 to 8.2 (3H, m) Enol form: 1.87 (3H, s), 3.65 (3H, s), 7.30 (1H, d, J=2.2Hz), 7.46 (1H, dd, J=2.2, 8.8Hz), 7.98 (1H, d, J=8.8Hz), 12.90 (1H, s)

Example 8

In a flask made of glass equipped with a stirrer, a thermometer, a reflux condenser and a dropping funnel and having an inner volume of 200 ml were charged 6.51 g (47.2 mmol) of potassium carbonate, 20 ml of N,N-dimethylformamide, 6.24 g (46.7 mmol) of dimethyl malonate with a purity of 99% and 5.00 g (30.8 mmol) of 2,4-difluoronitrobenzene with a purity of 98% under argon atmosphere, and under stirring, the mixture was reacted at room temperature for one hour and further by raising to 70° C. for 5 hours. After completion of the reaction, the mixture was cooled to room temperature, 100 ml of ethyl acetate was added to the mixture, and 10.5 ml (62.8 mmol) of 6 mol/l hydrochloric acid was gradually added dropwise to the mixture while stirring. Then, after adding 50 ml of water to the reaction mixture, the organic layer was separated, and washed successively with 20 ml of water and 20 ml of a saturated saline solution in this order, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=9:1 (volume ratio)) to obtain 6.22 g (isolation yield: 73%) of dimethyl 2-(5-fluoro-2-nitro-phenyl)malonate as white crystals with a purity of 98% (areal percentage by high performance liquid chromatography).

Example 9

In a flask made of glass equipped with a stirrer, a thermometer, a reflux condenser and a dropping funnel and having an inner volume of 100 ml were charged 8.29 g (60.0 mmol) of potassium carbonate, 30 ml of acetonitrile, 8.09 g (60.0 mmol) of dimethyl malonate with a purity of 99% and 5.00 g (30.0 mmol) of 2,4-difluoronitrobenzene with a purity of 98% under argon atmosphere, and under stirring, the mixture was reacted at 70° C. for 10 hours. After completion of the reaction, the mixture was cooled to room temperature, 50 ml of toluene was added to the mixture, and 7.5 ml (90 mmol) of 12 mol/l hydrochloric acid was gradually added dropwise to the mixture while stirring. Then, the organic layer was separated, and washed successively with 20 ml of water and 20 ml of a saturated saline solution in this order, and dried over anhydrous magnesium sulfate. After filtration, this organic layer was analyzed (absolute quantitative method) by high performance liquid chromatography, it was found that 6.61 g (reaction yield: 81%) of dimethyl 2-(5-fluoro-2-nitrophenyl)malonate was formed.

Example 10

The same reaction as in Example 9 was carried out except for changing the organic solvent to tetrahydrofuran in Example 9. As a result, 6.65 g (reaction yield: 82%) of dimethyl 2-(5-fluoro-2-nitrophenyl)malonate was found to be formed.

Example 11

In a flask made of glass equipped with a stirrer, a thermometer, a reflux condenser and a dropping funnel and having an inner volume of 500 ml were charged 55.3 g (0.40 mol) of potassium carbonate, 200 ml of N,N-dimethylformamide, 54.0 g (0.40 mol) of dimethyl malonate with a purity of 98% and 32.5 g (0.20 mmol) of 2,4-difluoronitrobenzene with a purity of 98% under argon atmosphere, and under stirring, the mixture was reacted at 70° C. for 3 hours. After completion of the reaction, the mixture was cooled to room temperature, 160 ml of toluene was added to the mixture, and 50 ml (0.60 mol) of 12 mol/l hydrochloric acid was gradually added dropwise to the mixture while stirring. Then, the organic layer was separated, and washed successively with 50 ml of water and 50 ml of a saturated saline solution in this order, and dried over anhydrous magnesium sulfate. After filtration, this organic layer was analyzed (absolute quantitative method) by high performance liquid chromatography, it was found that 45.3 g (reaction yield: 84%) of dimethyl 2-(5-fluoro-2-nitrophenyl)malonate was formed.

Example 12

In a flask made of glass equipped with a stirrer, a thermometer, a reflux condenser and a dropping funnel and having an inner volume of 100 ml were charged 3.03 g (21.9 mmol) of potassium carbonate, 5.0 ml of N,N-dimethylformamide, 2.17 g (21.7 mmol) of methyl cyanoacetate with a purity of 99% and 1.45 g (8.94 mmol) of 2,4-difluoronitrobenzene with a purity of 98% under argon atmosphere, and under stirring, the mixture was reacted at 60° C. for 6 hours. After completion of the reaction, the mixture was cooled to room temperature, 50ml of ethyl acetate was added to the mixture, and 2.9 ml (34.8 mmol) of 12 mol/l hydrochloric acid was gradually added dropwise to the mixture while stirring. Then, the organic layer was separated, and washed successively with 20 ml of water and 30 ml a saturated saline solution in this order, and dried over anhydrous magnesium sulfate. After filtration, the filtrate was concentrated under reduced pressure, and the resulting concentrate was purified by silica gel column chromatography (filler: Daisogel 1002W, eluent: toluene) to obtain 1.81 g (isolation yield: 84%) of methyl 2-(5-fluoro-2-nitrophenyl)-2-cyanoacetate as a yellowish oily product with a purity of 99% (areal percentage by high performance liquid chromatography).

Example 13

In a flask made of glass equipped with a stirrer, a thermometer, a reflux condenser and a dropping funnel and having an inner volume of 100 ml were charged 8.68 g (62.9 mmol) of potassium carbonate, 20 ml of N,N-dimethylformamide, 7.30 g (62.2 mmol) of methyl acetoacetate with a purity of 99% and 5.00 g (30.8 mmol) of 2,4-difluoronitrobenzene with a purity of 98% under argon atmosphere, and under stirring, the mixture was reacted at 25° C. for 5 hours. After completion of the reaction, the mixture was cooled to room temperature, 100 ml of ethyl acetate was added to the mixture, and 15.7 ml (94.2 mmol) of 6 mol/l hydrochloric acid was gradually added dropwise to the mixture while stirring. Then, after adding 50 ml of water to the mixture, the organic layer was separated, and washed successively with 20 ml of water and 30 ml of a saturated saline solution in this order, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=9:1 (volume ratio)) to obtain 6.08 g (isolation yield: 76%) of methyl 2-(5-fluoro-2-nitrophenyl)-2-acetoacetate as a yellowish oily product with a purity of 98% (areal percentage by high performance liquid chromatography)

Example 14

In a flask made of glass equipped with a stirrer, a thermometer, a reflux condenser and a dropping funnel and having an inner volume of 200 ml were charged 7.13 g (51.6 mmol) of potassium carbonate, 20 ml of N,N-dimethylformamide, 5.06 g (50.6 mmol) of methyl cyanoacetate with a purity of 99% and 5.00 g (25.8 mmol) of 2,4-dichloronitrobenzene with a purity of 99% under argon atmosphere, and under stirring, the mixture was reacted at 45° C. for 4 hours. After completion of the reaction, the mixture was cooled to room temperature, 100 ml of ethyl acetate was added to the mixture, and 12.9 ml (77.4 mmol) of 6 mol/l hydrochloric acid was gradually added dropwise to the mixture while stirring. Then, after adding 50 ml of water to the mixture, the organic layer was separated, and washed with 50 ml of a saturated saline solution, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=20:1 (volume ratio)) to obtain 5.76 g (isolation yield: 83%) of methyl 2-(5-chloro-2-nitrophenyl)-2-cyanoacetate as white crystals with a purity of 95% (areal percentage by high performance liquid chromatography).

Example 15

In a flask made of glass equipped with a stirrer, a thermometer, a reflux condenser and a dropping funnel and having an inner volume of 200 ml were charged 7.13 g (51.6 mmol) of potassium carbonate, 20 ml of N,N-dimethylformamide, 6.05 g (51.6 mmol) of methyl acetoacetate with a purity of 99% and 5.00 g (25.8 mmol) of 2,4-dichloronitrobenzene with a purity of 99% under argon atmosphere, and under stirring, the mixture was reacted at 70° C. for 3 hours. After completion of the reaction, the mixture was cooled to room temperature, 100 ml of ethyl acetate was added to the mixture, and 12.9 ml (77.4 mmol) of 6 mol/l hydrochloric acid was gradually added dropwise to the mixture while stirring. Then, after adding 30 ml of water to the mixture, the organic layer was separated, and washed with 30 ml of a saturated saline solution, and dried over anhydrous magnesium sulfate. After filtration, the filtrate was concentrated under reduced pressure, and the resulting concentrate was purified by silica gel column chromatography (filler: Daisogel 1002W, eluent: hexane:ethyl acetate=40:1 (volume ratio)) to obtain 4.33 g (isolation yield: 61%) of methyl 2-(5-chloro-2-nitrophenyl)-2-acetoacetate as a yellowish oily product with a purity of 98% (areal percentage by high performance liquid chromatography).

Example 16

In a flask made of glass equipped with a stirrer, a thermometer and a gas inlet tube and having an inner volume of 100 ml were charged 3.93 g (14.2 mmol) of dimethyl -2-(5-fluoro-2-nitrophenyl)malonate synthesized according to Example 1 with a purity of 98%, 0.5 g (0.12 mmol as a palladium atom) of 5% by weight palladium/carbon (49% hydrated product) and 50 ml of ethyl acetate under argon atmosphere. Then, the inner system was replaced with hydrogen, and the mixture was reacted under a hydrogen pressure of 0.15 MPa at 20° C. for 2 hours. After completion of the reaction, the catalyst was filtered off by filtrating the reaction mixture and then the filtrate was concentrated under reduced pressure, and the resulting concentrate was purified by silica gel column chromatography (filler: Daisogel 1002w, eluent: chloroform) to obtain 2.76 g (isolation yield: 92%) of 5-fluoro-3-methoxycarbonyloxindole as white crystals with a purity of 99% (areal percentage by high performance liquid chromatography).

5-Fluoro-3-methoxycarbonyloxindole is a novel compound having the following physical properties. Incidentally, from an integral valculus value by $^1$H-NMR, a keto form and an enol form existed in heavy chloroform with a ratio of 1:2.2.

Melting point; 142 to 143° C. EI-MS (m/e); 209 (M+), CI-MS (m/e); 210 (M+1) FT-IR (KBr method, cm$^{-1}$) ;3300 to 2600, 1647, 1569, 1481, 1204, 1160, 1108 $^1$H-NMR (CDCl$_3$, δ (ppm)); keto form: 3.82 (3H, s), 4.48 (1H, s), 6.81 to 6.88 (1H, m) 6.99 (1H, ddd, J=2.7, 8.5, 8.5Hz), 7.08 to 7.13 (1H, m), 8.18 (1H, s) enol form: 3.97 (3H, s), 6.81 to 6.88 (1H, m), 6.96 to 7.02 (1H, m), 7.39 (1H, dd, J=2.3, 9.4Hz), 8.24 (1H, s)

Example 17

In a flask made of glass equipped with a stirrer, a thermometer, a reflux condenser and a gas inlet tube and having an inner volume of 500 ml were charged 60.0 g (0.22mol) of dimethyl 2-(5-fluoro-2-nitrophenyl)malonate synthesized according to Example 1 with a purity of 98% and 228 g of methanol under argon atmosphere. Under stirring, while maintaining the temperature of the mixture to 40 to 45° C., 3.0 g (0.72 mmol in terms of the palladium atom) of 5% by weight palladium/carbon (49% hydrated product) was added to the mixture. Then, while blowing hydrogen with a flow rate of 123 ml/min. and a normal pressure, the mixture was reacted at the same temperature for 3 hours. After completion of the reaction, the reaction mixture was filtered to remove the catalyst, the filtrate was concentrated under reduced pressure, and 80 ml of methanol and 240 ml of water were added to the resulting concentrate and cooled to 10° C. Then, after filtration of the precipitated crystals, they were dried to obtain 54.5 g (isolation yield: 94%) of 5-fluoro-3-methoxy-carbonyloxindole as white crude crystals with a purity of 80% (analytical value by high performance liquid chromatography)

Example 18

In a flask made of glass equipped with a stirrer, a thermometer, a dropping funnel and a reflux condenser and having an inner volume of 500 ml were charged 26.5 g (0.10 mol) of crude crystal of 5-fluoro-3-methoxycarbonyloxindole synthesized according to Example 17 with a purity of 80% (analytical value by high performance liquid chromatography), 66.9 g of methanol and 52.0 ml (0.31 mol) of 6 mol/l hydrochloric acid, and the mixture was reacted at 70 to 80° C. for 2 hours. After completion of the reaction, the mixture was cooled to room temperature, 55.0 ml (0.44 mol) of 8 mol/l aqueous sodium hydroxide solution was added to the mixture, and the resulting mixture was stirred at 40° C. for 30 minutes. Then, 8.3 ml (0.10 mol) of 12 mol/l hydrochloric acid was added to the resulting mixture. After removing methanol under reduced pressure, the reaction mixture was cooled to 0 to 5° C., then a solid was precipitated so that it was collected by filtration. The resulting solid was recrystallized from isopropyl alcohol/water to obtain 12.6 g (isolation yield: 80%) of 5-fluorooxindole as white crystals with a purity of 99% (areal percentage by high performance liquid chromatography).

Physical properties of 5-fluorooxindole were as follows.

Melting point; 141 to 142° C. EI-MS (m/e); 151(M+), CI-MS(m/e); 152(M+1) Elemental analysis; Carbon 63.56%, Hydrogen 4.02%, Nitrogen 9.29% (theoretical value ($C_8H_6NOF$); Carbon 63.57%, Hydrogen 4.00%, Nitrogen 9.27%) FT-IR (KBr method, $cm^{-1}$) ; 3400 to 2500, 1700, 1633, 1485, 1317, 1195, 745, 673, 591 $^1$H-NMR ($CDCl_3$, δ (ppm)); 3.56 (2H, s), 6.75 to 6.85 (1H, m) 6.85 to 7.00 (2H, m), 9.03 (1H, brs)

Utilizability in Industry

According to the present invention, a 2-(5-halogeno-2-nitrophenyl)-2-substituted acetic acid ester compound can be produced from a 2,4-dihalogenonitrobenzene compound with a simple and easy method, whereby an industrially suitable process for preparing a 2-(5-halogeno-2-nitrophenyl)-2-substituted acetic acid ester compound can be provided.

Moreover, according to the present invention, an industrially suitable process for preparing 5-fluorooxindole can be provided by a simple and easy method from an easily available 2-(5-fluoro-2-nitrophenyl)malonic acid diester to obtain 5-fluorooxindole with a high yield.

What is claimed is:

1. A process for preparing 5-fluorooxindole represented by the formula (3):

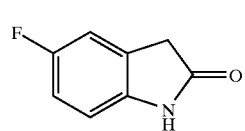

(3)

which comprises (A) cyclizing 2-(5-fluoro-2-nitrophenyl) malonic acid diester represented by the formula (1):

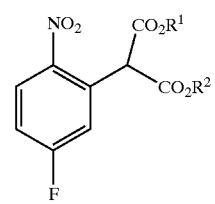

(1)

wherein $R^1$ and $R^2$ are the same or different from each other and each represents a group which does not participate in the reaction, and wherein $R^1$ and $R^2$ each represents an alkyl group having 1 to 10 carbon atoms, a cycloalkyl group having 3 to 7 carbon atoms, an aralkyl group having 7 to 10 carbon atoms or an aryl group having 6 to 14 carbon atoms, under reductive conditions to form a 5-fluorooxindole-3-carboxylic acid ester represented by the formula (2):

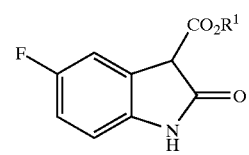

(2)

wherein $R^1$ has the same meaning as defined above, in a first step, and (B) then, decarboxylating the 5-fluorooxindole-3-carboxylic acid ester in a second step.

2. The process for preparing 5-fluorooxindole according to claim 1, wherein the cyclization under the reductive conditions of the first step is carried out under a hydrogen atmosphere in the presence of a catalyst.

3. The process for preparing 5-fluorooxindole according to claim 2, wherein the catalyst is a material containing at least one metal atom selected from the group consisting of palladium, platinum and nickel.

4. The process for preparing 5-fluorooxindole according to claim 1, wherein the decarboxylation of the second step is carried out in the presence of an acid.

5. The process for preparing 5-fluorooxindole according to claim 2, wherein the catalyst is in an amount of 0.01 to 1.0% by weight based on the amount of the 2-(5-fluoro-2-nitrophenyl)malonic acid diester.

6. The process for preparing 5-fluorooxindole according to claim 2, wherein the catalyst is in an amount of 0.05 to 0.5% by weight based on the amount of the 2-(5-fluoro-2-nitrophenyl)malonic acid diester.

7. The process for preparing 5-fluorooxindole according to claim 6, wherein the catalyst is selected from the group consisting of palladium/carbon, palladium/barium sulfate, palladium hydroxide/carbon, platinum/carbon, palladium-platinum/carbon, platinum oxide and Raney nickel.

8. The process for preparing 5-fluorooxindole according to claim 6, wherein the catalyst is palladium/carbon.

9. The process for preparing 5-fluorooxindole according to claim 2, wherein the first step is carried out at a pressure of 0.1 to 5 MPa and at a temperature of 20 to 80° C.

10. The process for preparing 5-fluorooxindole according to claim 2, wherein the first step is carried out at a pressure of 0.1 to 2 MPa and at a temperature of 30 to 60° C.

11. The process for preparing 5-fluorooxindole according to claim 4, wherein the acid is selected from the group consisting of hydrochloric acid, sulfuric acid, nitric acid, methanesulfonic acid and acetic acid.

12. The process for preparing 5-fluorooxindole according to claim 4, wherein the acid is hydrochloric acid or sulfuric acid.

13. The process for preparing 5-fluorooxindole according to claim 12, wherein the acid is in an amount of 1 to 10-fold moles based on the amount of the 5-fluorooxindole-3-carboxylic acid ester.

14. The process for preparing 5-fluorooxindole according to claim 12, wherein the acid is in an amount of 2 to 5-fold moles based on the amount of the 5-fluorooxindole-3-carboxylic acid ester.

15. The process for preparing 5-fluorooxindole according to claim 2, wherein the first step is carried out in the presense of at least one solvent selected from the group consisting of water, methanol, ethanol, methyl, acetate, ethyl acetate, benzene, toluene, tetrahydrofuran and dioxane.

16. The process for preparing 5-fluorooxindole according to claim 15, wherein the solvent is selected from the group consisting of water, methanol and ethanol.

17. The process for preparing 5-fluorooxindole according to claim 16, wherein the catalyst is in an amount of 3 to 50-fold weight based on the amount of the 2-(5-fluoro-2-nitrophenyl)malonic acid diester.

18. The process for preparing 5-fluorooxindole according to claim 15, wherein the second step is carried out in the presence of at least one solvent selected from the group consisting of water, methanol, ethanol, n-butyl alcohol, t-butyl alcohol, tetrahydrofuran, dioxane, cyclohexane and toluene.

19. The process for preparing 5-fluorooxindole according to claim 18, wherein the solvent in the second step is selected from the group consisting of water, methanol and ethanol.

20. The process for preparing 5-fluorooxindole according to claim 19, wherein the solvent in the second step is in an amount of 2 to 20-fold weight based on the amount of the 5-fluorooxindole-3-carboxylic acid ester.

\* \* \* \* \*